(12) United States Patent
Crain et al.

(10) Patent No.: US 6,328,251 B1
(45) Date of Patent: *Dec. 11, 2001

(54) VEHICLE-SHAPED DENTAL FLOSS DISPENSER AND METHOD THEREFOR

(75) Inventors: Jon S. Crain, Las Vegas, NV (US); Elias Tamez, P.O. Box 532, Mabton, WA (US) 98935, part interest to each

(73) Assignees: Elias Tamez, Mabton, WA (US); Eric J. Longan, Las Vegas, NV (US)

(*) Notice: Subject to any disclaimer, the term of this patent is extended or adjusted under 35 U.S.C. 154(b) by 0 days.

This patent is subject to a terminal disclaimer.

(21) Appl. No.: 09/453,584

(22) Filed: Dec. 7, 1999

Related U.S. Application Data

(63) Continuation of application No. 29/108,297, filed on Jul. 23, 1999, now Pat. No. Des. 429,382.

(51) Int. Cl.[7] .......................... B65H 49/00; B65H 75/28; B65H 49/18
(52) U.S. Cl. ..................................... 242/588.6; 242/588.3; 242/580; 242/128; 242/137.1; D28/66
(58) Field of Search ............................. 242/588.6, 588.3, 242/580, 580.1, 128, 137.1, 134; D28/65, 66, 67, 68; D3/20, 21

(56) References Cited

U.S. PATENT DOCUMENTS

| | | | |
|---|---|---|---|
| D. 311,259 | * 10/1990 | Smith | D28/67 |
| D. 381,468 | * 7/1997 | Dolan et al. | D28/66 |
| D. 429,382 | * 8/2000 | Crain et al. | D28/67 |
| D. 431,879 | * 10/2000 | Perlin | D28/67 |
| 5,566,872 | * 10/1996 | Dolan et al. | 242/588.6 X |

* cited by examiner

*Primary Examiner*—Donald P. Walsh
*Assistant Examiner*—Minh-Chau Pham
(74) *Attorney, Agent, or Firm*—Harry M. Weiss; Weiss & Moy, P.C.

(57) ABSTRACT

A dental floss dispenser having the external appearance of an automobile. The dispenser includes a cavity accessible by inverting the dispenser, which cavity receives a spool of dental floss. The dental floss is then dispensed through an opening in the cavity, which opening exits in the engine compartment of the automobile. The engine compartment may be opened for accessing the dental floss, and then closed after use, so that the floss is not visible to an observer.

5 Claims, 1 Drawing Sheet

VEHICLE-SHAPED DENTAL FLOSS DISPENSER AND METHOD THEREFOR

RELATED APPLICATION

This is a Continuation of U.S. Ser. No. 29/108,297, filed Jul. 23, 1999, now U.S. Pat. No. Des. 429,382 in the name of the applicant of this application.

BACKGROUND OF THE INVENTION

1. Field of the Invention

This invention relates generally to dental floss dispensing devices and methods and, more specifically, to a vehicle-shaped dental floss dispenser and method.

2. Background of the Invention

The dental health benefits associated with the regular use of dental floss are well-known and essentially universally accepted. Nevertheless, many people do not floss regularly, for a variety of reasons. Often, people fail to floss because a floss dispenser is not readily at hand when the person is brushing his or her teeth or otherwise attending to his or her dental health needs.

Over the years, some efforts have been made to develop dental floss dispensers having greater convenience and greater aesthetic appeal, presumably in the belief that such qualities would make a person more likely to position floss in a location where it would be likely to be used. For example, U.S. Pat. No. 5,097,964, issued to Fitz discloses a dental floss dispenser in the shape of a "toothed character," wherein a dental floss spool is positioned within the character through a bottom portion thereof, and floss is passed out of the character's hand and cut at the character's teeth. While the device disclosed in Fitz is more aesthetically pleasing than non-decorative dispensers, the feature of having the floss pass outside of the character in an exposed manner makes it apparent that the "toothed character" is a floss dispenser. Moreover, a toothed character is not necessarily the type of decorative object that one commonly sees as a house decoration, particularly in rooms outside of the bathroom. For these reasons, a user may not be comfortable displaying the dispenser on a counter or other public space within the house—and particularly not in a public space outside of a bathroom. Thus, notwithstanding its aesthetic qualities, the dispenser of Fitz may also not be used as frequently as desired for good dental health, in those instances where it is concealed from view in a draw or cabinet. Further limiting the utility of the dispenser of Fitz is the fact that it is dimensioned to carry only one size of floss at any particular time, making it unsuitable for efficient use by two persons requiring different types of floss.

Therefore, a need existed to provide a floss dispenser that is aesthetically pleasing in appearance, while effectively concealing to the unsuspecting eye that it is in fact a floss dispenser. The outer configuration of the floss dispenser should, moreover, be of a type commonly seen in decorative objects displayed in a home, including in rooms other than the bathroom. The floss dispenser should further, preferably, be dimensioned to simultaneously carry more than one floss spool, so that more than one type of floss may be dispensed therethrough without the need for "reloading" the dispenser.

SUMMARY OF THE INVENTION

It is an object of the present invention to provide a dental floss dispenser that is aesthetically pleasing in appearance, while effectively concealing to the unsuspecting eye that it is in fact a floss dispenser.

It is a further object of the present invention to provide a dental floss dispenser having an outer configuration of a type commonly seen in decorative objects displayed in a home, including in rooms other than the bathroom.

It is a still further object of the present invention to provide a dental floss dispenser that is dimensioned to simultaneously carry more than one floss spool.

BRIEF DESCRIPTION OF THE PREFERRED EMBODIMENTS

In accordance with one embodiment of the present invention, a dental floss dispenser is disclosed. The dental floss dispenser comprises, in combination: an automobile-shaped decorative holding structure; wherein the holding structure has the outer configuration of an automobile and includes a closeable engine compartment; a cavity located within the holding structure and dimensioned to receive a dental floss spool; wherein the cavity is not visible when the holding structure is in an upright portion; at least one dental floss spool rotatably secured in the cavity; an opening located in the cavity and dimensioned to receive therethrough the strand of dental floss, wherein the opening leads to the closeable engine compartment.

In accordance with another embodiment of the present invention, a method for providing a dental floss dispenser is disclosed. The method comprises the steps of: providing an automobile-shaped decorative holding structure; wherein the holding structure has the outer configuration of an automobile and includes a closeable engine compartment; providing a cavity located within the holding structure and dimensioned to receive a dental floss spool; wherein the cavity is not visible when the holding structure is in an upright portion; rotatably securing at least one dental floss spool in the cavity; providing an opening located in the cavity and dimensioned to receive therethrough the strand of dental floss, wherein the opening leads to the closeable engine compartment.

The foregoing and other objects, features, and advantages of the invention will be apparent from the following, more particular, description of the preferred embodiments of the invention, as illustrated in the accompanying drawings.

DETAILED DESCRIPTION OF THE PREFERRED EMBODIMENTS

Referring to FIGS. 1–6 and 9, reference number 10 refers generally to one embodiment of the automobile-shaped dental floss dispenser 10 (hereinafter "dispenser 10") of the present invention. The dispenser 10 comprises a vehicle body 12. While the vehicle body 12 shown in these Figures is in the shape of a four-door sedan, essentially any vehicle shape may be utilized to comprise the vehicle body 12 without departing from the spirit or scope of this invention.

Figure 1:
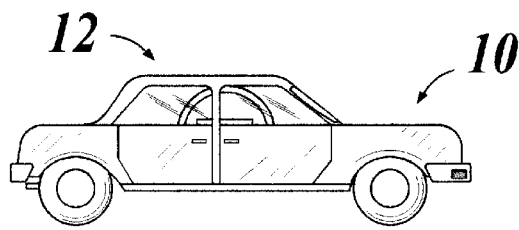
FIG. 1 is a right side elevational view of the dental floss dispenser of the present invention.
Figure 2:
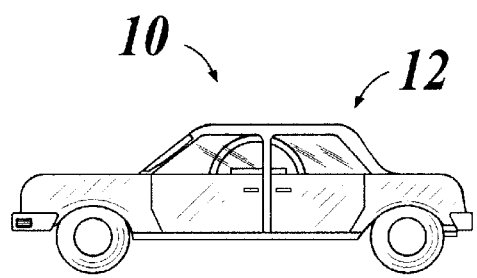
FIG. 2 is a left side elevational view of the dental floss dispenser of FIG. 1.
Figure 3:
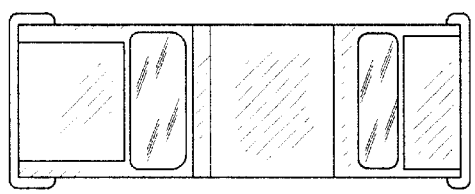
FIG. 3 is a top view of the dental floss dispenser of FIG. 2.
Figure 4:
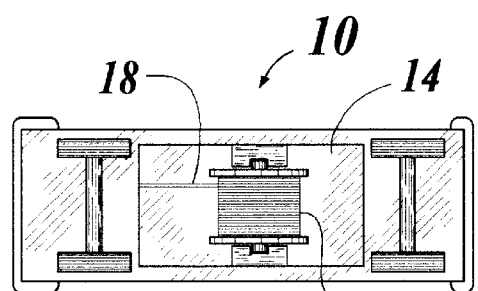
FIG. 4 is a bottom view of the dental floss dispenser of FIG. 1 with a bottom central portion open to show a spool of floss retained therein.
Figure 5:
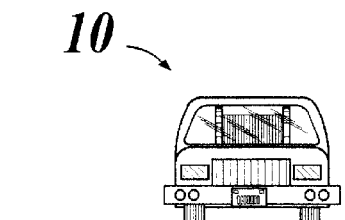
FIG. 5 is a front view of the dental floss dispenser of FIG. 1.
Figure 7:
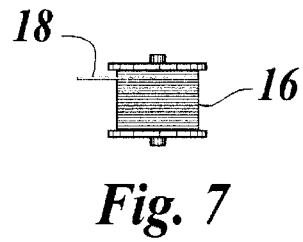
FIG. 7 is a top view of the dental floss spool as shown in FIG. 4.
Figure 8:
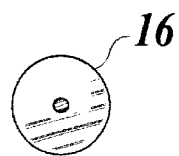
FIG. 8 is a side elevational view of one side of the dental floss spool as shown in FIG. 4.
Figure 6:
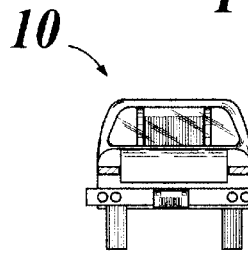
FIG. 6 is a rear view of the dental floss dispenser of FIG. 1.

Referring now to FIGS. 4, 7–8, the vehicle body 12 comprises a dental floss spool compartment 14 (hereinafter compartment 14) located in an interior portion of the vehicle body 12. The compartment 14 may be accessed by, as shown in FIG. 4, approaching the compartment 14 from the bottom of the vehicle body 12. The compartment 14 is dimensioned to rotatably receive a dental floss spool 16.

Figure 9:
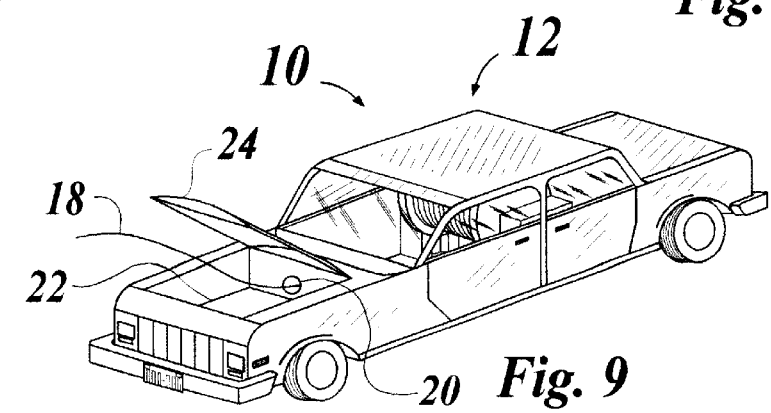
FIG. 9 is a perspective view of the dental floss dispenser of FIG. 1 with the front hood open to permit the dental floss to be pulled out for use by a person.

Referring now to FIGS. 4 and 9, once the dental floss spool 16 is rotatably positioned within the compartment 14, a length of floss 18 may be threaded through an opening 20 that permits access from the compartment 14 through to an engine compartment 22. the engine compartment 22 may be sealed, and thus any view of the length of floss 18 is blocked, by closing the hood 24. In this manner, a person viewing the dispenser 10 with the hood 24 in the closed position (see, e.g., FIGS. 1–3, 5–6) would not necessarily have any indication that the vehicle body 12 comprised a floss dispenser. When a person desires to use the dispenser 10 to obtain a length of floss 18, the hood 24 is opened and the length of floss 18 is extracted.

It is also possible, without departing from the spirit or scope of the present invention, to dispense the length of floss 18 through an opening located in any portion of the vehicle body 12, including a bottom portion thereof, other than the engine compartment 22.

While the invention has been particularly shown and described with reference to preferred embodiments thereof, it will be understood by those skilled in the art that the foregoing and other changes in form and details may be made therein without departing from the spirit and scope of the invention.

What is claimed is:

1. A dental floss dispenser comprising:

a decorative holding structure:

wherein said holding structure has the outer configuration of an automobile and includes a closeable compartment;

a cavity located within said holding structure and dimensioned to receive a dental floss spool:

wherein said cavity is not visible when said holding structure is in an upright portion;

at least one dental floss spool rotatably secured in said cavity;

an opening located in said cavity and dimensioned to receive therethrough said strand of dental floss, wherein said opening leads to said closeable compartment.

2. The dental floss dispenser of claim 1, wherein said holding structure has the configuration of a four-door sedan.

3. A dental floss dispenser comprising:

a decorative holding structure:

wherein said holding structure has the outer configuration of an automobile;

a cavity located within said holding structure and dimensioned to receive a dental floss spool;

wherein said cavity is not visible when said holding structure is in an upright portion;

at least one dental floss spool rotatably secured in said cavity;

An opening located in said cavity and dimensioned to receive therethrough said strand of dental floss, wherein said opening leads to an outer portion of said decorative holding structure.

4. A method for providing a dental floss dispenser comprising the steps of:

providing a decorative holding structure;

wherein said holding structure has the outer configuration of an automobile and includes a closeable compartment;

providing a cavity located within said holding structure and dimensioned to receive a dental floss spool;

wherein said cavity is not visible when said holding structure is in an upright portion;

rotatably securing at least one dental floss spool in said cavity;

providing an opening located in said cavity and dimensioned to receive therethrough said strand of dental floss, wherein said opening leads to said closeable compartment.

5. The method of claim 4, wherein said holding structure has the configuration of a four-door sedan.

* * * * *